United States Patent
Jung et al.

(10) Patent No.: US 10,947,174 B2
(45) Date of Patent: Mar. 16, 2021

(54) METHOD FOR PREPARING TRIMETHYLOLPROPANE

(71) Applicant: LG CHEM, LTD., Seoul (KR)

(72) Inventors: Dawon Jung, Daejeon (KR); Sungshik Eom, Daejeon (KR); Tae Yun Kim, Daejeon (KR); Dong Hyun Ko, Daejeon (KR); Mi Young Kim, Daejeon (KR); Min Ji Choi, Daejeon (KR); Taewoo Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/472,493

(22) PCT Filed: Oct. 4, 2018

(86) PCT No.: PCT/KR2018/011742
§ 371 (c)(1),
(2) Date: Jun. 21, 2019

(87) PCT Pub. No.: WO2019/083188
PCT Pub. Date: May 2, 2019

(65) Prior Publication Data
US 2020/0189998 A1 Jun. 18, 2020

(30) Foreign Application Priority Data
Oct. 23, 2017 (KR) .................. 10-2017-0137495

(51) Int. Cl.
*C07C 29/141* (2006.01)
*C07C 45/64* (2006.01)

(52) U.S. Cl.
CPC ............ *C07C 29/141* (2013.01); *C07C 45/64* (2013.01)

(58) Field of Classification Search
CPC ....... C07C 29/141; C07C 45/64; C07C 29/94; C07C 31/22; C07C 45/45; C07C 45/78; C07C 47/19; B01J 8/02; B01J 23/72
See application file for complete search history.

(56) References Cited

U.S. PATENT DOCUMENTS

| | | | |
|---|---|---|---|
| 6,018,074 A | 1/2000 | Kratz et al. | |
| 6,187,971 B1 | 2/2001 | Kratz et al. | |
| 7,253,326 B1 | 8/2007 | Eom et al. | |
| 2003/0139631 A1 | 7/2003 | Muller et al. | |
| 2004/0044256 A1* | 3/2004 | Dernbach | C07C 29/141 568/799 |
| 2004/0082821 A1 | 4/2004 | Koch et al. | |
| 2007/0282135 A1 | 12/2007 | Maas et al. | |
| 2008/0167506 A1* | 7/2008 | Sirch | C07C 29/141 568/862 |
| 2009/0069604 A1* | 3/2009 | Maas | C07C 31/245 568/465 |
| 2012/0004472 A1 | 1/2012 | Sirch et al. | |
| 2012/0245394 A1* | 9/2012 | Tompers | B01J 23/78 568/853 |

FOREIGN PATENT DOCUMENTS

| | | | |
|---|---|---|---|
| KR | 1999-0067461 A | 8/1999 | |
| KR | 2003-0057363 A | 7/2003 | |
| KR | 10-0499599 B1 | 7/2005 | |
| KR | 10-2007-0091726 A | 9/2007 | |
| KR | 10-0839292 B1 | 6/2008 | |
| KR | 10-2008-0100280 A | 11/2008 | |
| KR | 10-1470038 B1 | 12/2014 | |
| KR | 10-2017-0012572 A | 2/2017 | |
| WO | WO 1998028253 * | 7/1998 | ........... C07C 29/141 |

* cited by examiner

*Primary Examiner* — Rosalynd A Keys
(74) *Attorney, Agent, or Firm* — Dentons US LLP

(57) ABSTRACT

A method for preparing trimethylolpropane, the method including: subjecting dimethylolbutanal (DMB) to a hydrogenation reaction in the presence of a metal catalyst and an alcohol solvent. During the hydrogenation reaction, a weight ratio of the alcohol solvent based to dimethylolbutanal is 2 to 10.

6 Claims, 3 Drawing Sheets

[Figure 1]
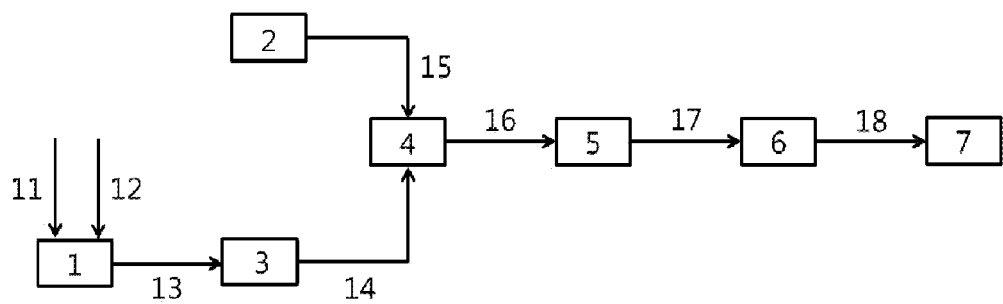
[Figure 2]
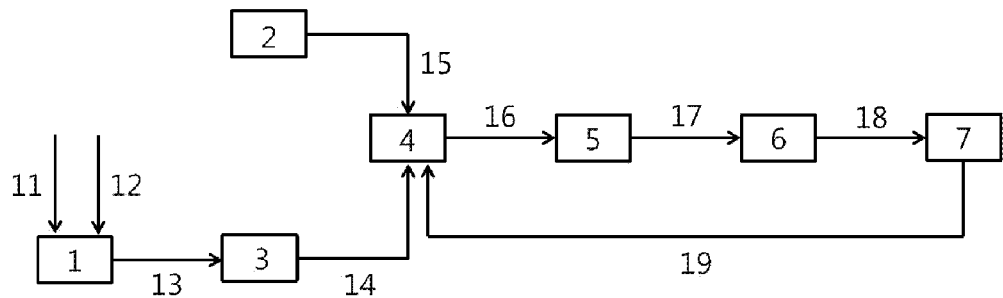

[Figure 3]
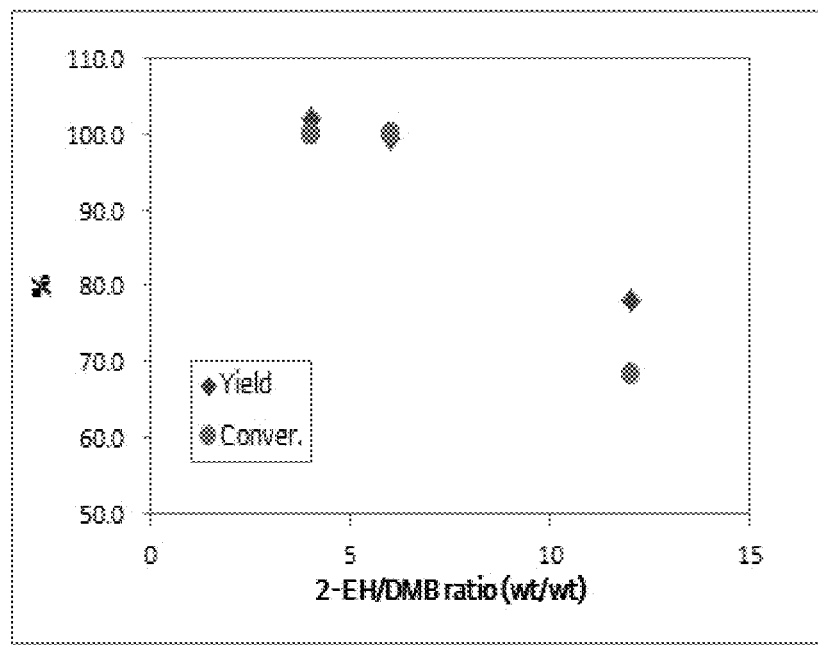
[Figure 4]
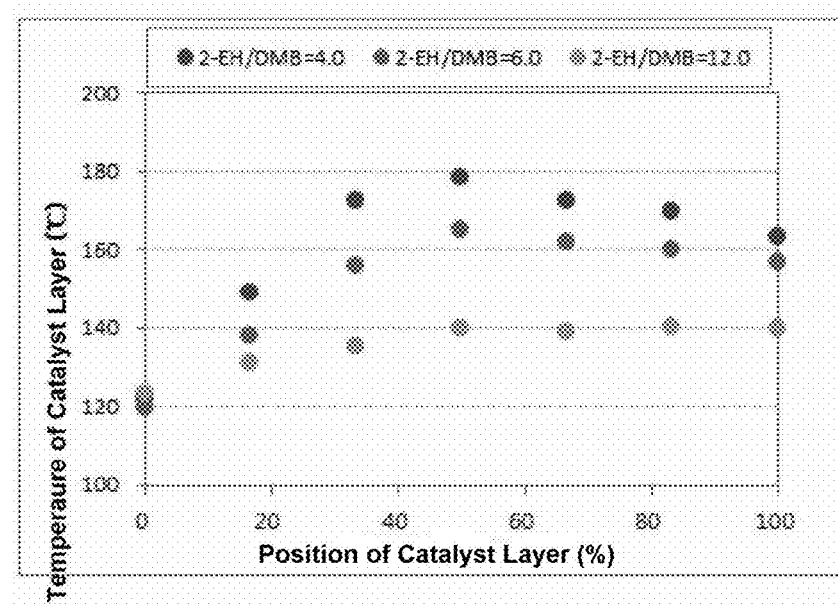

[Figure 5]
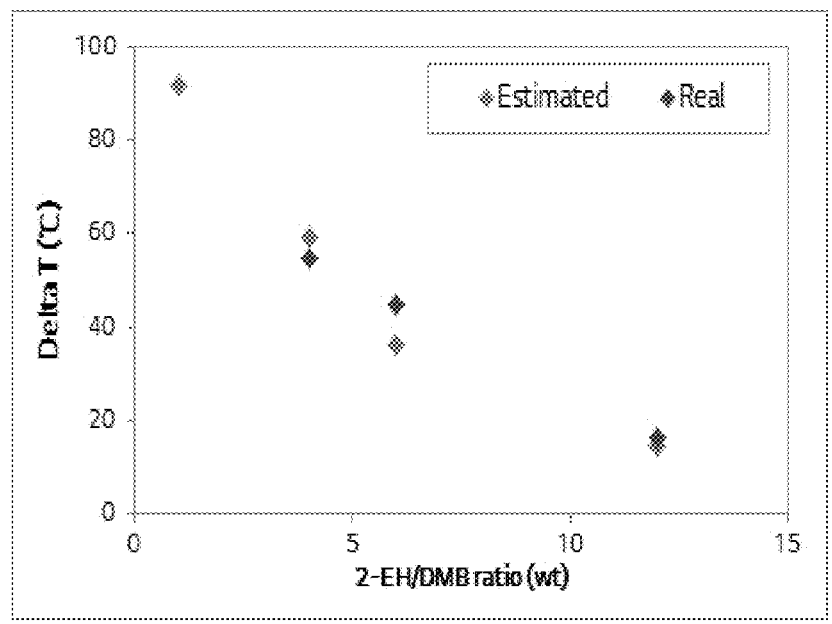

METHOD FOR PREPARING TRIMETHYLOLPROPANE

CROSS-REFERENCE TO RELATED APPLICATIONS

This application is a National Stage Application of International Application No. PCT/KR2018/011742 filed Oct. 4, 2018, and claims priority to and the benefit of Korean Patent Application No. 10-2017-0137495 filed in the Korean Intellectual Property Office on Oct. 23, 2017, the entire contents of which are incorporated herein by reference.

TECHNICAL FIELD

The present specification relates to a preparation method of trimethylolpropane.

BACKGROUND ART

Trimethylolpropane (TMP) may be prepared by various methods, and one of the methods is performed by Cannizzaro Reaction.

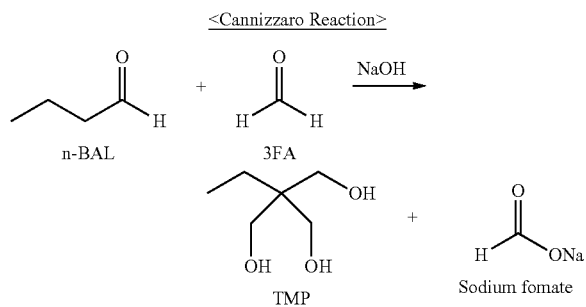

<Cannizzaro Reaction>

In this case, trimethylolpropane is prepared by using an alkali metal base, but one equivalent of a formate salt is produced as a byproduct together, so that Cannizzaro Reaction is not efficient.

Trimethylolpropane is a white crystalline substance at room temperature, and is widely used as a raw material in various fields such as alkyd resin, saturated polyester, synthetic lubricant, polyurethane resin, and plasticizer fields. Accordingly, studies for producing trimethylolpropane, which is an industrially important raw material, by an economical method have been continuously conducted.

BRIEF DESCRIPTION OF DRAWINGS

FIG. 1 is a process diagram for performing a preparation method of trimethylolpropane according to an exemplary embodiment of the present specification.

FIG. 2 is a process diagram for performing a preparation method of trimethylolpropane according to another exemplary embodiment of the present specification.

FIG. 3 is a graph illustrating a TMP yield and a DMB conversion rate according to Examples 1 and 2 and Comparative Example 1 of the present specification.

FIG. 4 is a graph illustrating a catalyst layer temperature profile according to Examples 1 and 2 and Comparative Example 1 of the present specification.

FIG. 5 is a graph illustrating ΔT according to Examples 1 and 2 and Comparative Examples 1 and 3 of the present specification.

EXPLANATION OF REFERENCE NUMERALS AND SYMBOLS

1: Reaction raw material
2: Hydrogen storage tank
3: Heater
4: Reactor
5: Heat exchanger
6: Pump
7: Storage tank
11, 12, 13, 14, 15, 16, 17, 18, 19: Pipe

DETAILED DESCRIPTION OF THE INVENTION

Technical Problem

The present specification provides a preparation method of trimethylolpropane.

Technical Solution

An exemplary embodiment of the present specification provides a preparation method of trimethylolpropane, the preparation method including:
preparing trimethylolpropane (TMP) by subjecting dimethylolbutanal (DMB) to a hydrogenation reaction under a metal catalyst and an alcohol solvent,
in which during the hydrogenation reaction, a weight ratio of the alcohol solvent based on dimethylolbutanal is 2 to 10.

Advantageous Effects

By the preparation method of trimethylolpropane according to an exemplary embodiment of the present specification, trimethylolpropane with high yield can be obtained.

BEST MODE

Hereinafter, the present specification will be described in more detail.

In the present specification, the 'yield (%)' is defined as a value obtained by dividing the weight of trimethylolpropane, which is a product of a hydrogenation reaction, by the weight of dimethylolbutanal which is a raw material of the hydrogenation reaction. For example, the yield may be represented by the following equation.

Yield (%)=Δ$TMP$/Reactant $DMB$×100

In the present specification, the 'conversion rate (%)' refers to a rate at which a reactant is converted into a product, and for example, the DMB conversion rate may be defined by the following equation.

DMB conversion rate (%)=100×(1−Product $DMB$/Reactant $DMB$)

In the present specification, the 'selectivity (%)' is defined as a value obtained by dividing the change amount of TMP by the change amount of DMB. For example, the selectivity may be represented by the following equation.

Selectivity (%)=Δ$TMP$/Δ$DMB$×100=yield×100/conversion rate

An exemplary embodiment of the present specification provides a preparation method of trimethylolpropane, the preparation method including: preparing trimethylolpropane (TMP) by subjecting dimethylolbutanal (DMB) to a hydrogenation reaction under a metal catalyst and an alcohol solvent, in which during the hydrogenation reaction, a weight ratio of the alcohol solvent based on dimethylolbutanal is 2 to 10.

According to an exemplary embodiment of the present specification, during a hydrogenation reaction of DMB separated after an aldol condensation reaction, the heat of reaction may be removed and the hydrogenation reactivity may be improved by adding an alcohol solvent to adjust the ratio of alcohol solvent/DMB in the raw material.

In particular, when the amount of the alcohol solvent in the hydrogenation reaction raw material is small, it is difficult to control the heat of reaction, and when the amount thereof is equal to or more than an appropriate level, the DMB conversion rate and the TMP yield are reduced, and the service life of the catalyst is shortened. Accordingly, the inventors of the present application have found that in consideration of the control of the heat of reaction and the hydrogenation reactivity, during a process of preparing TMP by subjecting DMB to a hydrogenation reaction, the TMP yield can be maximized when the weight ratio (alcohol solvent/DMB) of the alcohol solvent based on dimethylolbutanal is 2 to 10.

According to an exemplary embodiment of the present specification, the alcohol solvent during the hydrogenation reaction may be an alcohol solvent having 2 to 10 carbon atoms. Specifically, the alcohol solvent during the hydrogenation reaction may be an alcohol solvent having 6 to 8 carbon atoms, and may be preferably an alcohol solvent having 8 carbon atoms.

According to an exemplary embodiment of the present specification, the alcohol solvent may be 2-ethyl hexanol (2-EH).

According to an exemplary embodiment of the present specification, during the hydrogenation reaction, the weight ratio (alcohol solvent/DMB (g/g)) of the alcohol solvent based on dimethylolbutanal may be 2 to 10. Preferably, the weight ratio may be 2 to 8. More preferably, the weight ratio may be 3 to 7.

Specifically, when the weight ratio of the alcohol solvent based on dimethylolbutanal is decreased to less than 2, it is difficult to control the heat of reaction while the change in temperature (delta T, $\Delta T$) of a reactor is increased to 80° C. or more. In this case, there is a risk that while the heat of reaction and the heat of heating may be combined to cause a runaway reaction, and the capacity of a circulator for controlling heat needs to be increased. There is a disadvantage in that this ultimately leads to an investment cost burden at the time of commercialization. In contrast, when the weight ratio of the alcohol solvent based on dimethylolbutanal is increased to more than 10, the time for DMB to stay in a catalyst layer becomes short, so that the DMB conversion rate and the TMP yield are remarkably decreased. In addition, as the weight ratio (alcohol solvent/DMB) is increased, a hotspot section showing the maximum active section of the catalyst is also pushed by a rear part of the catalyst layer, thereby ultimately affecting the service life of the catalyst.

According to an exemplary embodiment of the present specification, the metal catalyst may be a copper (Cu)-based metal catalyst. As the copper-based metal catalyst, it is possible to use a catalyst obtained by allowing a CuO content of 10 wt % to 40 wt %, a $SiO_2$ content of 55 wt % to 85 wt %, and a BaO content of 5 wt % to react. In this case, a pre-treatment process using $H_2$ and heat needs to be performed for the hydrogenation reaction. The copper-based metal catalyst is not limited as long as the copper-based metal catalyst is used for the hydrogenation reaction.

According to an exemplary embodiment of the present specification, a reactor used for the preparation method of trimethylolpropane is a reactor used for the hydrogenation reaction, and is not limited thereto, but may be preferably a fixed bed reactor (FBR), and more preferably a fixed bed reactor (FBR) with an L/D (a value obtained by dividing a height (L) of a reaction section (bed) by a diameter (D) thereof) of 20 to 40.

According to an exemplary embodiment of the present specification, the reaction temperature of the hydrogenation reaction may be 80° C. to 160° C., preferably 100° C. to 140° C., and more preferably 110° C. to 130° C.

According to an exemplary embodiment of the present specification, the reaction pressure of the hydrogenation reaction may be 20 bar to 70 bar. Preferably, the reaction pressure may be 25 bar to 50 bar.

According to an exemplary embodiment of the present specification, during the hydrogenation reaction, the molar ratio of hydrogen ($H_2$) based on dimethylolbutanal may be 1 to 3. Preferably, the molar ratio may be 1 to 2.

According to an exemplary embodiment of the present specification, the preparing of the trimethylolpropane may include preparing trimethylolpropane with a yield of 98% or more. Specifically, the preparing of the trimethylolpropane may include preparing trimethylolpropane with a yield of 98.3% or more. Trimethylolpropane with high yield can be prepared by adjusting the reaction conditions, the specific alcohol solvent, the weight ratio of the alcohol solvent and DMB, and the like in the hydrogenation reaction.

According to an exemplary embodiment of the present specification, the preparation method of trimethylolpropane may further include, after the preparing of the trimethylolpropane by the hydrogenation reaction, purifying the prepared trimethylolpropane.

The preparation method of trimethylolpropane according to an exemplary embodiment of the present specification may further include: (A) preparing a dimethylolbutanal (DMB) mixed product by subjecting n-butyraldehyde (n-BAL) and formaldehyde (FA) to an aldol condensation reaction under an alkylamine catalyst; and (B) separating dimethylolbutanal from the dimethylolbutanal mixed product.

In particular, in the case of the Cannizzaro Reaction of preparing TMP, a formate salt is produced together as a byproduct while TMP is produced from n-BAL by the reaction. However, in the preparation method of trimethylolpropane according to the present specification, after the aldol condensation reaction, DMB is separated, and then TMP is produced via the hydrogenation process, so that the byproduct is not produced.

According to an exemplary embodiment of the present specification, during the aldol condensation reaction in Step (A), for the content of the reactant, formaldehyde and the alkylamine catalyst may be 200 parts by weight to 500 parts by weight and 1 part by weight to 30 parts by weight, respectively, based on 100 parts by weight of n-butyraldehyde, and more preferably, formaldehyde and the alkylamine catalyst may be 250 parts by weight to 400 parts by weight and 10 parts by weight to 20 parts by weight, respectively, based on 100 parts by weight of n-butyraldehyde.

Further, according to an exemplary embodiment of the present specification, the alkylamine catalyst in Step (A) is alkylamine having 3 to 20 carbon atoms, and specifically, trimethylamine, triethylamine (TEA), tributylamine, and the like may be used, and preferably, triethylamine may be used.

According to an exemplary embodiment of the present specification, the reaction temperature in Step (A) may be preferably 20° C. to 70° C., and more preferably 25° C. to 50° C. The reaction time is preferably 90 minutes to 200 minutes.

In addition, according to an exemplary embodiment of the present specification, in the preparing of the dimethylolbutanal mixed product in Step (A), stirring the product simultaneously with the aldol condensation reaction may be performed. That is, the reaction and the stirring may be simultaneously performed. In this case, the stirring temperature may be 20° C. to 70° C., and more preferably 25° C. to 50° C. The stirring speed may be 150 rpm to 350 rpm, and more preferably 200 rpm to 300 rpm.

According to an exemplary embodiment of the present specification, the dimethylolbutanal mixed product obtained as a result of Step (A) may include DMB, TMP, FA, and water. In this case, the weight ratio of DMB and TMP included in the dimethylolbutanal mixed product may be 2:1 to 6:1, and more preferably 3:1 to 4:1. The product may include water.

According to an exemplary embodiment of the present specification, the separating of the dimethylolbutanal in Step (B) may adopt a distillation or extraction method, but the method is not limited thereto.

According to an exemplary embodiment of the present specification, the method may further include purifying dimethylolbutanal after the separating of the dimethylolbutanal in Step (B).

Furthermore, according to an exemplary embodiment of the present specification, when the extraction method is used in the separating of the dimethylolbutanal in Step (B), a counter-current type extraction apparatus may be used as the extraction apparatus, and the extraction may be a multistage extraction including two or more stages, but the extraction and the extraction method are not limited thereto.

According to an exemplary embodiment of the present specification, when the extraction method is used in the separating of the dimethylolbutanal in step (B), the extraction temperature is preferably 20° C. to 75° C., specifically, the extraction temperature is preferably 25° C. to 70° C., and more specifically, the extraction temperature is preferably 50° C. to 70° C. In addition, the extraction time is preferably 30 minutes to 90 minutes.

The preparation process of trimethylolpropane according to an exemplary embodiment of the present specification will be schematically illustrated as follows:

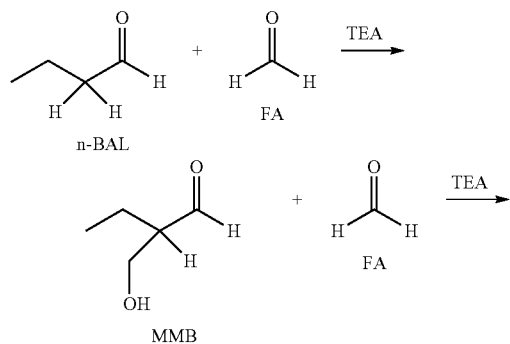

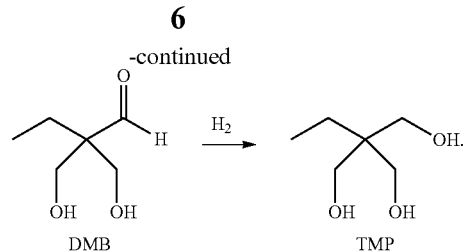

FIG. 1 is an exemplary process diagram of apparatuses and pipes for performing the preparation method of trimethylolpropane according to an exemplary embodiment of the present specification.

According to FIG. 1, dimethylolbutanal and the alcohol solvent are introduced into a reaction raw material 1 through a pipe 11 and a pipe 12, respectively. In this case, the alcohol solvent may be an alcohol solvent having 2 to 10 carbon atoms, preferably an alcohol solvent having 8 carbon atoms, and more preferably 2-ethyl hexanol. The dimethylolbutanal may be obtained via a series of separation processes after the aldol condensation reaction. The series of separation processes may be extraction.

Next, the hydrogenation reaction raw material 1 is preheated in a heater 3 through a pipe 13 and supplied to a reactor 4 through a pipe 14, and hydrogen ($H_2$) required for the hydrogenation reaction in a hydrogen storage tank 2 is also supplied to the reactor 4 through a pipe 15. In this case, the reactor 4 is filled with a copper-based metal catalyst as a fixed bed. The reactor 4 is a reactor used for the hydrogenation reaction and is not limited, but may be preferably a fixed bed reactor (FBR) with an L/D (a value obtained by dividing a height (L) of a reaction section (bed) by a diameter (D) thereof) of 20 to 40.

Alumina balls at the inlet and outlet of the reactor 4 supports a catalyst layer in the middle of the reactor 4, and twelve temperature sensors are inserted at constant intervals, and thus show a temperature profile. By employing the inlet temperature of the catalyst layer as a hydrogenation reaction temperature, the reaction temperature is set to 80° C. to 160° C., and the reaction pressure is set to 20 bar to 70 bar. During the hydrogenation reaction, $H_2$/DMB (mol/mol) and the weight hourly space velocity (WHSV) are set to conditions of 1 to 3 and 0.3 $h^{-1}$ to 0.7 $h^{-1}$, respectively. In this case, the hydrogenation reaction is performed by setting the weight ratio of the alcohol solvent, based on DMB in the hydrogenation reactant injected into the reactor 4, to the condition of 2 to 10.

Next, the TMP produced by the hydrogenation reaction in the reactor 4 is discharged through a pipe 16, cooled through a heat exchanger 5, and then discharged from the heat exchanger 5 through a pipe 17. Subsequently, the cooled TMP is stored in a storage tank 7 through a pipe 18 by a pump 6.

FIG. 2 is an exemplary process diagram of apparatuses and pipes for performing a preparation method of trimethylolpropane according to another exemplary embodiment of the present specification.

According to FIG. 2, a small amount of a portion of the product including unreacted DMB may flow into the storage tank 7. In this case, in order to control the conversion of the unreacted DMB and the heat of reaction of the hydrogenation reaction, a portion of the product including unreacted DMB in the storage tank 7 may flow into the reactor 4 through a pipe 19 and re-circulated.

As described above, according to an exemplary embodiment of the present specification, in the process of preparing TMP from DMB through a hydrogenation reaction during the preparation method of TMP, the yield of TMP may be maximized by selecting an optimal hydrogenation reaction solvent (alcohol solvent) and adjusting the weight ratio of DMB and the alcohol solvent.

MODE FOR INVENTION

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

Examples

Preparation Example 1

Dimethylolbutanal (DMB) was prepared by extracting an aldol condensation reaction product reacting at a molar ratio of FA/n-BAL=4 in a 10-L jacket type reactor.

Example 1

A hydrogenation raw material was formulated by adding 2-ethyl hexanol (2-EH) to the DMB obtained in Preparation Example 1.

Thereafter, TMP was prepared by a hydrogenation reaction by introducing the formulated raw material into a fixed bed reactor (FBR) with an L/D (a value obtained by dividing a height (L) of a reaction section (bed) by a diameter (D) thereof) of 30, which was filled with a copper-based metal catalyst.

In this case, the weight ratio (2-EH/DMB) of 2-EH based on DMB was 4. During the hydrogenation reaction, the number of moles of the added hydrogen and the weight hourly space velocity (WHSV) were set to $H_2$/DMB (mol/mol)=1.5 and 0.3 $h^{-1}$, respectively. Alumina balls at the inlet and outlet of the reactor supported a catalyst layer in the middle of the reactor, and twelve temperature sensors were inserted at constant intervals, and thus showed a temperature profile. An experiment was performed at 120° C. by setting the inlet temperature of the catalyst layer to a reaction temperature, and the reaction pressure was set to 30 bar.

Example 2

TMP was prepared in the same manner as in Example 1, except that in Example 1, the weight ratio (2-EH/DMB) of 2-EH based on DMB was 6.

Example 3

TMP was prepared in the same manner as in Example 1, except that in Example 1, the weight ratio (2-EH/DMB) of 2-EH based on DMB was 10.

Comparative Example 1

TMP was prepared in the same manner as in Example 1, except that in Example 1, the weight ratio (2-EH/DMB) of 2-EH based on DMB was 12.

Comparative Example 2

TMP was prepared in the same manner as in Example 1, except that in Example 1, 1-hexanol was used instead of 2-ethyl hexanol, and the weight ratio (1-hexanol/DMB) of 1-hexanol based on DMB was 4.

The TMP yields obtained in Examples 1 to 3 and Comparative Examples 1 and 2, the DMB conversion rates, and the TMP selectivities were calculated by the following equations, and the results of measuring the change in temperature (delta T, $\Delta T=T_{out}-T_{in}$, that is, means the heat of reaction) according to the temperature profile of the catalyst layer are shown in the following Table 1.

The TMP yields and the DMB conversion rates, the temperature profile of the catalyst layer, and $\Delta T$ according to Examples 1 and 2 and Comparative Example 1 are illustrated in FIG. 3, FIG. 4, and FIG. 5, respectively.

TMP yield (%)=$\Delta$TMP/Reactant DMB×100

DMB conversion rate (%)=100×(1−Product DMB/Reactant DMB)

TMP Selectivity (%)=$\Delta$TMP/$\Delta$DMB×100=yield×100/conversion rate

TABLE 1

| Classification | Solvent | Solvent/DMB | TMP yield (%) | DMB conversion rate (%) | TMP selectivity (%) | Δ T (° C.) |
|---|---|---|---|---|---|---|
| Example 1 | 2-EH | 4 | 99.1 | 100 | 99.1 | 55 |
| Example 2 | 2-EH | 6 | 98.3 | 100 | 98.3 | 44.9 |
| Example 3 | 2-EH | 10 | 98.6 | 100 | 98.6 | 21.6 |
| Comparative Example 1 | 2-EH | 12 | 68.8 | 74.7 | 92.1 | 14.6 |
| Comparative Example 2 | 1-Hexanol | 4 | 90.9 | 94.9 | 95.8 | — |

Comparative Example 3

TMP was prepared in the same manner as in Example 1, except that in Example 1, the weight ratio (2-EH/DMB) of 2-EH based on DMB was 1.

However, a result that $\Delta T$(° C.) was 92.0° C. was obtained by assuming the TMP yield, the DMB conversion rate, and the TMP selectivity to be 100% and using the calculated values, and through the result, the heat of reaction was predicted.

The delta T ($\Delta T$(° C.)) was calculated through the following Equation (1) and Equation (2). The Q value was calculated by using Equation (2), which is an Arrhenius equation, based on the experimental value of the reaction rate according to the reaction temperature.

$$Q=\Sigma Cp_i * m_i * \Delta T_i \quad \text{[Equation (1)]}$$

(Q: the heat of reaction, i: each composition component, Cp: the heat capacity value of each composition component, and m: the mass value of each composition of the product of the hydrogenation reaction)

$$r=A*e^{-Ea/RT} \quad \text{[Equation (2)]}$$

(r: the reaction rate, T: absolute temperature, R: the gas constant, A: the frequency coefficient or frequency factor, and Ea: the activation energy, and here, is equal to the Q value)

According to Examples 1 to 3 and Comparative Examples 1 to 3, when trimethylolpropane (TMP) was prepared by subjecting dimethylolbutanal (DMB) to a hydrogenation reaction under a copper-based metal catalyst and 2-EH, TMP with high yield could be obtained when the weight ratio of 2-EH based on DMB was 2 to 10.

Further, according to the temperature profile of the catalyst layer and ΔT, it was confirmed that when the 2-EH/DMB was 4 to 10, the heat of reaction was easily controlled, and the investment cost burden could be reduced because the capacity of the heat exchanger was relatively small as compared to when the 2-EH/DMB was 1 or less.

In the case of Comparative Example 3 (2-EH/DMB=1), the heat of reaction was predicted by assuming the TMP yield, the DMB conversion rate, and the TMP selectivity to be 100% and using the calculated values, and as the ΔT (delta T) value was increased, there is a tendency that the TMP yield and the TMP selectivity are lowered due to the generated heat. Since the calculated ΔT in Comparative Example 3 was 92.0° C., which is remarkably higher than those in Examples 1 to 3, it is possible to sufficiently expect that the TMP yield and the TMP selectivity will become lower than those in Examples 1 to 3.

Consequently, it could be confirmed that during the hydrogenation reaction of DMB separated after the aldol condensation reaction, the heat of reaction could be removed and the hydrogenation reactivity could be improved by adding 2-EH and adjusting the ratio of 2-EH/DMB in the raw material, thereby maximizing the TMP yield.

Although the preferred exemplary embodiments of the present invention have been described above, the present invention is not limited thereto, and various modifications can be made and carried out within the scope of the claims and the detailed description of the invention, and also fall within the scope of the invention.

The invention claimed is:

1. A method for preparing trimethylolpropane, the method comprising:
    subjecting dimethylolbutanal to a hydrogenation reaction in the presence of a metal catalyst and an alcohol solvent,
    wherein the alcohol solvent is 2-ethylhexanol,
    wherein a weight ratio of the alcohol solvent to dimethylolbutanal is 4 to 10, and
    wherein the metal catalyst is a copper-based metal catalyst.

2. The preparation method of claim 1, wherein a reaction temperature of the hydrogenation reaction is 80° C. to 160° C.

3. The preparation method of claim 1, wherein a reaction pressure of the hydrogenation reaction is 20 bar to 70 bar.

4. The preparation method of claim 1, wherein during the hydrogenation reaction, a molar ratio of hydrogen to dimethylolbutanal is 1 to 3.

5. The preparation method of claim 1, wherein a yield of trimethylolpropane is 98% or more.

6. The preparation method of claim 1, further comprising:
    (A) preparing a dimethylolbutanal mixed product by subjecting n-butyraldehyde and formaldehyde to an aldol condensation reaction in the presence of an alkylamine catalyst; and
    (B) separating dimethylolbutanal from the dimethylolbutanal mixed product.

* * * * *